US006171296B1

(12) United States Patent
Chow

(10) Patent No.: US 6,171,296 B1
(45) Date of Patent: Jan. 9, 2001

(54) FLOW DIRECTED CATHETER

(75) Inventor: Sean L. Chow, Tustin, CA (US)

(73) Assignee: MicroTherapeutics, Inc., San Clemente, CA (US)

( * ) Notice: Under 35 U.S.C. 154(b), the term of this patent shall be extended for 0 days.

(21) Appl. No.: 09/066,861

(22) Filed: Apr. 28, 1998

(51) Int. Cl.⁷ ................................................. A61M 25/00
(52) U.S. Cl. ............................................. 604/525; 604/526
(58) Field of Search ................................... 604/525, 526, 604/264, 280–282, 523, 524, 527; 600/433–435; 138/125, 127, 129, 144

(56) References Cited

U.S. PATENT DOCUMENTS

| | | | |
|---|---|---|---|
| 3,416,531 | * 12/1968 | Edwards | 604/281 |
| 3,485,234 | * 12/1969 | Stevens | 604/282 |
| 3,498,286 | * 3/1970 | Polanyi et al. | 604/281 |
| 3,935,857 | 2/1976 | Co . | |
| 3,948,273 | 4/1976 | Sanders . | |
| 4,254,774 | 3/1981 | Boretos . | |
| 4,277,432 | 7/1981 | Woinowski . | |
| 4,490,421 | 12/1984 | Levy . | |
| 4,577,543 | 3/1986 | Wilson . | |
| 4,579,555 | 4/1986 | Russo . | |
| 4,739,768 | 4/1988 | Engelson . | |
| 4,840,623 | 6/1989 | Quackenbush . | |
| 4,842,590 | 6/1989 | Tanabe et al. . | |
| 4,848,344 | 7/1989 | Sos et al. . | |
| 4,876,140 | 10/1989 | Quackenbush . | |
| 4,886,506 | 12/1989 | Lovgren et al. . | |
| 4,898,591 | * 2/1990 | Jang et al. | 604/264 |
| 4,900,314 | 2/1990 | Quackenbush . | |
| 4,998,923 | 3/1991 | Samson et al. . | |
| 5,085,649 | 2/1992 | Flynn . | |
| 5,104,388 | 4/1992 | Quackenbush . | |
| 5,104,705 | 4/1992 | Quackenbush . | |
| 5,125,913 | 6/1992 | Quackenbush . | |
| 5,176,660 | 1/1993 | Truckai . | |
| 5,234,416 | * 8/1993 | Macaulay et al. | 604/282 |
| 5,254,107 | * 10/1993 | Soltesz | 604/525 |
| 5,270,086 | 12/1993 | Hamlin . | |
| 5,273,536 | 12/1993 | Savas . | |
| 5,282,785 | 2/1994 | Shapland et al. . | |
| 5,290,306 | 3/1994 | Trotta et al. . | |
| 5,308,342 | 5/1994 | Sepetka et al. . | |
| 5,312,356 | 5/1994 | Engelson et al. . | |
| 5,334,146 | 8/1994 | Ozasa . | |
| 5,336,205 | 8/1994 | Zenzen et al. . | |
| 5,338,298 | 8/1994 | McIntyre . | |
| 5,338,299 | 8/1994 | Barlow . | |

(List continued on next page.)

FOREIGN PATENT DOCUMENTS

| | | |
|---|---|---|
| 4306136 | 9/1994 | (DE) . |
| 2506106 | 11/1982 | (FR) . |
| 1651864 | 5/1991 | (SU) . |
| WO 91/07203 | 5/1991 | (WO) . |

* cited by examiner

Primary Examiner—Sharon Kennedy
(74) Attorney, Agent, or Firm—Burns, Doane, Swecke, & Mathis, LLP

(57) ABSTRACT

A flow directed microcatheter is formed having a gradually changing flexibility and diameter between a proximal end and a distal end of the microcatheter. The changing properties of the microcatheter according to the present invention provide the flexibility of the distal tip needed to allow the microcatheter to be directed by the flow of blood within the vasculature, and the columnar strength and torquability at the proximal end and along the length of the microcatheter needed to advance and direct the distal tip to the target site. A proximal segment of the microcatheter includes a plurality of strands which vary in diameter to change the flexibility of the microcatheter. A distal segment of the microcatheter includes an inner layer which is compatible with solvents, such as DMSO, and an outer layer which provides strength and flexibility. The proximal segment and the distal segment of the microcatheter are joined by a kink resistant fuse joint.

13 Claims, 1 Drawing Sheet

U.S. PATENT DOCUMENTS

| | | |
|---|---|---|
| 5,358,493 | 10/1994 | Schweich, Jr. et al. . |
| 5,378,230 | 1/1995 | Mahurkar . |
| 5,411,477 | 5/1995 | Saab . |
| 5,456,774 | 10/1995 | Bos et al. . |
| 5,458,570 | 10/1995 | May, Jr. . |
| 5,462,523 * | 10/1995 | Samson et al. ............ 604/30 |
| 5,474,537 | 12/1995 | Solar . |
| 5,484,424 * | 1/1996 | Cottenceau et al. ............ 604/525 |
| 5,503,631 | 4/1996 | Onishi et al. . |
| 5,514,236 * | 5/1996 | Avellanet et al. ............ 156/154 |
| 5,525,388 | 6/1996 | Wand et al. . |
| 5,531,715 | 7/1996 | Engelson et al. . |
| 5,533,985 | 7/1996 | Wang . |
| 5,538,512 | 7/1996 | Zenzon et al. . |
| 5,542,937 | 8/1996 | Chee et al. . |
| 5,545,151 * | 8/1996 | O'Connor et al. ............ 604/264 |
| 5,599,326 | 2/1997 | Carter . |
| 5,730,733 * | 3/1998 | Mortier et al. ............ 604/280 |
| 5,836,925 * | 11/1998 | Soltesz ............ 604/264 |
| 5,836,926 * | 11/1998 | Peterson et al. ............ 604/264 |
| 5,843,050 * | 12/1998 | Jones et al. ............ 604/167 |
| 5,851,203 * | 12/1998 | Van Muiden ............ 604/282 |
| 5,899,892 * | 5/1999 | Mortier et al. ............ 604/280 |
| 5,911,715 * | 6/1999 | Berg et al. ............ 604/525 |
| B2 4,739,768 | 10/1995 | Engelson . |

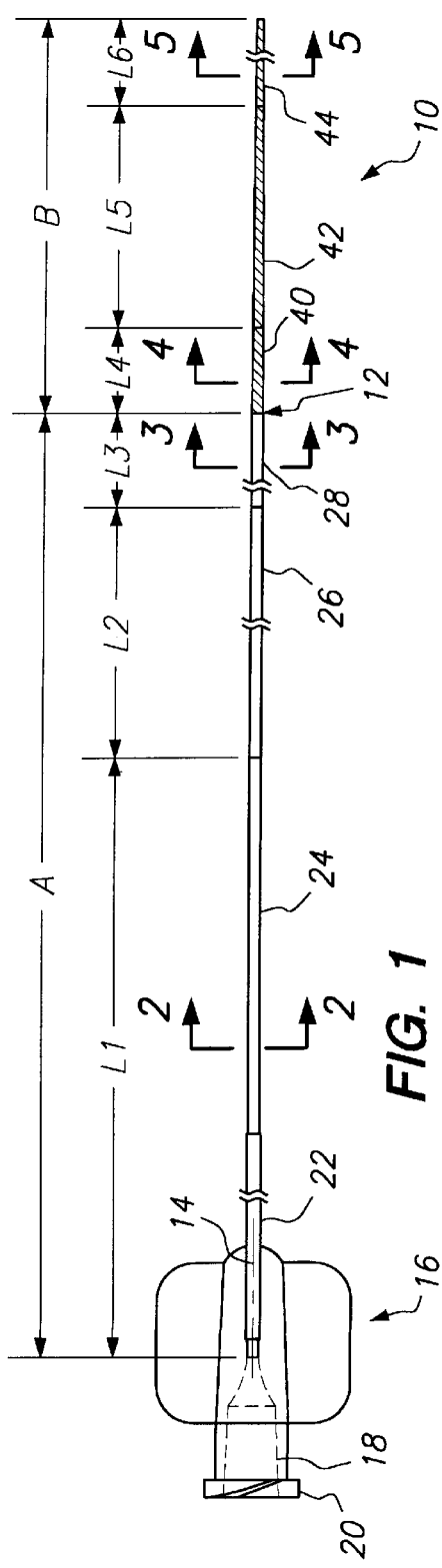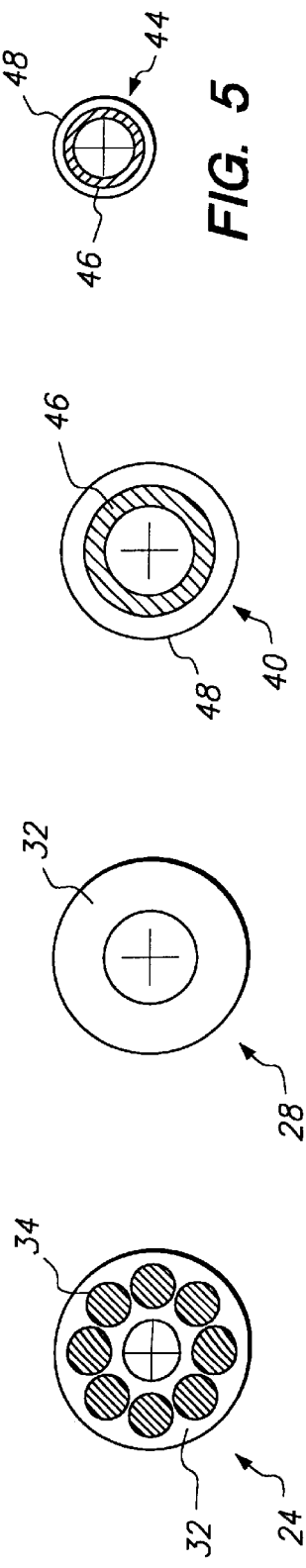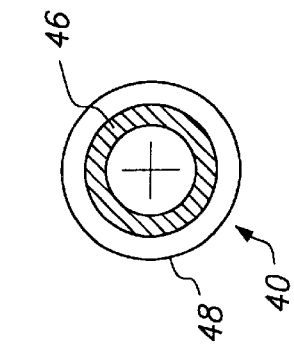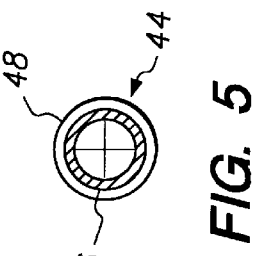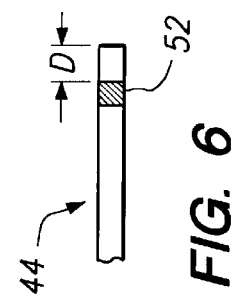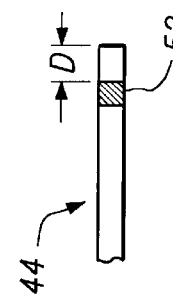

FLOW DIRECTED CATHETER

BACKGROUND OF THE INVENTION

1. Field of the Invention

The invention relates to a catheter for delivery of beneficial agents to a target site, and more particularly, the invention relates to a DMSO compatible, flow directed microcatheter for delivery of beneficial agents to a target site in the vasculature.

2. Brief Description of the Related Art

Microcatheters are used to deliver beneficial agents such as diagnostic, therapeutic, or occlusive agents to a target site within the vasculature. When a catheter is to be inserted into the various small blood vessels of the brain, heart, kidneys, etc., which are far away from the catheter insertion point and require passage of the catheter through many twists and turns of the vasculature, microcatheters are used which are able to access these various small blood vessels. Microcatheters may be either tracked with a guidewire to the target site or may be flow directed.

A guidewire directed catheter is provided with a guidewire within the lumen of the catheter to assist in advancing the catheter through the vasculature. Typically, a guidewire and catheter are inserted together into an artery such as the femoral artery and the guidewire and catheter are pushed and twisted to navigate the catheter from the artery to a target site. Once a distal tip of the catheter has been placed at a target site, the guidewire is then removed to allow injection of a beneficial agent through the lumen of the catheter. The process of tracking a catheter to a target site with a guidewire becomes increasing difficult as the guidewire, catheter, and target vessel become very small, particularly, when the target site is deep within the vasculature and involves a highly tortuous path for access.

Accordingly, flow directed catheters may be used when it is necessary to reach a target site deep within the vasculature. One type of flow directed catheter includes a highly flexible catheter having an inflatable, pre-punctured balloon at a distal tip. The balloon is continuously reinflated and carried by blood flow in the vasculature to the target site. The flow directed balloon catheter is extremely flexible at the distal tip to allow the balloon to carry the catheter through the vasculature. The extreme flexibility of the catheter distal tip results in difficulty in advancing the catheter from the proximal end without causing buckling.

Another type of flow directed catheter includes a flexible distal tip which is directed to a target site as a result of the blood flowing to the site. These flow directed catheters must have sufficient columnar strength to allow the catheter to be advanced to the target site by pushing the catheter from a proximal end. Additionally, the flow directed catheter must have a tip which is flexible enough to navigate the tortuous blood vessel pathways while having sufficient pushability to allow the catheter to be advanced, and having sufficient burst strength to withstand injection pressures.

In order to achieve the objectives of flexibility, strength, and pushability, flow directed microcatheters have generally been formed of polyurethane. However, polyurethane is undesirable for the delivery of many beneficial agents including solvents because many solvents will have the tendency to dissolve polyurethane by pulling plasticizers and loose radicals out of the polyurethane.

An example of a beneficial agent including a solvent which is delivered to a target site within the vasculature is a liquid embolic composition used for the treatment of arterial venous malformations (AVMs), tumors, intercranial aneurysms, and the like. One type of liquid embolic composition used for treatment of, e.g., AVMs includes a water soluble biocompatible, non-biodegradable polymer dissolved in a biocompatible solvent. The liquid embolic composition can be used for prevention of bleeding, prevention of blood supply to tumors, as well as for blocking blood flow within aneurysms, and many other uses. As the liquid embolic composition is delivered to the target site via the microcatheter, the solvent dissipates from the polymer material of the liquid embolic composition causing the polymer material within the target site to solidify occluding an AVM, blood vessel, aneurysms, or other vascular abnormality. However, when delivery of the liquid embolic composition is attempted via conventional prior art polyurethane microcatheters, the catheter will swell and/or dissolve during use.

Accordingly, it would be desirable to provide a flow directed catheter with sufficient strength and flexibility to be inserted in a flow directed manner into tortuous paths of the vasculature which is compatible with the delivery of a beneficial agent including a solvent, such DMSO (dimethylsulfoxide). However, many materials which are compatible with various solvents including DMSO have insufficient flexibility and strength for use in the vary small diameter flow directed microcatheters.

SUMMARY OF THE INVENTION

The present invention relates to a flow directed microcatheter having a changing flexibility and diameter between a proximal end and a distal end of the microcatheter. The changing properties of the microcatheter according to the present invention provide the flexibility of the distal tip needed to allow the microcatheter to be directed by the flow of blood within the vasculature and the columnar strength and torquability at the proximal end and along the length of the microcatheter needed to advance and direct the distal tip to the target site.

In accordance with one aspect of the present invention, a flow directed microcatheter is compatible with various solvents including DMSO.

In accordance with another aspect of the present invention, a flow directed microcatheter includes a proximal segment, a hub connected to a first end of the proximal segment, a distal segment, and a joint formed between a second end of the proximal segment and a first end of the distal segment. The proximal segment has a first end, a second end, and a lumen extending along a length of the proximal segment between the first and second ends. The proximal segment has a substantially constant outer diameter and a substantially constant inner diameter along the length of the proximal segment, and has a flexibility which changes between the first and second ends without distinct joints between the first and second end. The distal segment has a first end, a second end, and a lumen extending along a length of the distal segment between the first and second ends. The distal segment has an inner layer formed of a first material and an outer layer formed of a second material having a higher burst strength than that of the inner layer. The distal segment tapers from a first diameter at the first end to a second diameter at the second end such that the flexibility of the distal segment allows the microcatheter to be guided by a flow of blood without the use of a guidewire.

In accordance with a further aspect of the present invention, a flow directed microcatheter includes a proximal segment having a first end, a second end, and a lumen extending along a length of the proximal segment between the first and second ends, the proximal segment formed of a material which is compatible with DMSO, and a distal segment having a first end, a second end, and a lumen extending between the first and second ends, the first end of the distal segment connected to the second end of the proximal segment. The distal segment includes an inner layer formed of a first material which is compatible with DMSO, the inner layer having an inner layer flexibility and an inner layer strength, and an outer layer formed of a second material having an outer layer flexibility and an outer layer strength which are greater than the inner layer flexibility and the inner layer strength.

According to another further aspect of the present invention, a flow directed microcatheter includes a first segment having a gradually changing flexibility between a first end and a second end and a lumen extending from the first end to the second end, a second segment having a gradually changing flexibility and a gradually changing diameter between a first end and a second end, wherein the second end of the first segment and the first end of the second segment have a durometer and diameter which are substantially the same, and a kink resistant joint formed between the second end of the first segment and the first end of the second segment the two segments formed by heat fusing.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a side elevational view of microcatheter according to the present invention;

FIG. 2 is a cross-sectional view taken along line 2—2 of FIG. 1 showing a first section of a proximal segment A of the microcatheter;

FIG. 3 is a cross-sectional view taken along line 3—3 of FIG. 1 showing a third section of the proximal segment A of the microcatheter;

FIG. 4 is a cross-sectional view taken along line 4—4 of FIG. 1 showing a first section of a distal segment B of the microcatheter;

FIG. 5 is a cross-sectional view taken along line 5—5 of FIG. 1 showing a third section of the distal segment B of the microcatheter; and FIG. 6 is an enlarged view of the distal tip of the microcatheter of FIG. 1.

DETAILED DESCRIPTION OF THE PREFERRED EMBODIMENTS

The flow directed microcatheter according to the present invention addresses the drawbacks of the known flow directed microcatheters by providing a microcatheter which can be tracked into treatment sites deep within the vasculature without the need for a guidewire and can be used with biocompatible solvents such as DMSO. The microcatheter 10 according to the present invention includes a proximal segment A connected to a distal segment B by a fuse joint 12. The proximal segment A and the distal segment B according to the present invention are formed with different structures and materials to achieve the strength, flexibility, and compatibility requirements for different portions of the microcatheter. The microcatheter will be described below with reference to the following defined terms.

"Microcatheter" means a catheter having a distal tip size of about 4 French or smaller.

"Strength" means both the ability of a catheter to resist fluid pressures applied to the lumen of the catheter without bursting or leaking, and the ability to resist tensile forces without tearing.

"Flexibility" means the ability of a catheter to bend when a force is applied in a direction other than along an axis of the catheter. The flexibility is inversely related to the amount of force required to deflect the catheter from an initial position.

"DMSO compatible" means the ability to withstand contact with DMSO for a period of time long enough to perform an intervascular procedure without significant degradation of the material which would affect the strength or fluid impermeability of the material.

Examples of DMSO compatible materials and some of the preferred durometers of these materials for use in the microcatheter according to the present invention include polyolefins, such as, polyethylene (80A–80D), polyester polyether block copolymer (30D–80D), Alcryn (chlorinated polyolefin) (60A–80A), Pebax (polyamide polyether block copolymer) (25D–70D); fluoropolymers, such as, PTFE (polytetrafluoroethylene, such as Teflon), perfluoroalkoxy resin, fluorinated ethylene propylene polymers, ETFE, and SEBS (styrene ethylene butadiene styrene); silicones; interpenetrating networks of silicone; nylons (6/6, 6/10, and 6/12); and polyamide. Other materials compatible with DMSO can be readily determined by the skilled artisan.

DMSO or other solvent compatibility of a material for use in a catheter can be tested by the following procedure. A catheter formed of a material for which compatibility is to be determined is tested to determine burst and tensile strength of the material. The catheter is then immersed in the solvent for a period of time between 1 minute and several hours, preferably about 30 minutes. The catheter is then tested again to determine the burst and tensile strength of the material after soaking and the properties are compared. If no substantial change in property has occurred, the material is compatible with the solvent.

The microcatheter 10 according to the present invention has a changing flexibility, diameter, and strength between a proximal end and a distal tip of the microcatheter. The changing properties of the microcatheter according to the present invention provide the flexibility of the distal tip needed to allow the microcatheter to be directed by the flow of blood within the vasculature and the columnar strength and torquability at the proximal end and along the length of the microcatheter needed to advance and direct the distal tip to the target site. The changing properties along the length of the microcatheter are provided by both changes in material and changes in cross sectional dimensions and construction of the microcatheter within and between the proximal and distal segments.

As described above, the proximal segment A is connected to the distal segment B by the fuse joint 12. A first end 14 of the proximal segment A is connected to a hub 16. The hub 16 includes an interior luer taper 18 and a flange 20 having a thread for connection to a fluid delivery device such as a syringe. Examples of suitable syringe/hub combinations are disclosed in U.S. Ser. No. 08/866,208, for "Contoured Syringe and Novel Luer Hub and Methods for Embolizing Blood Vessels" filed as Attorney Docket No. 018413-016 on Jun. 13, 1997 which application is incorporated herein by reference in its entirety.

The first end 14 of the proximal segment A is surrounded by a strain relief tube 22 which prevents kinking of the first end. The strain relief tube 22 and the first end 14 of the proximal segment A are bonded to the luer hub 16 in a known manner.

The proximal segment A has a varying cross sectional confirmation along its length. In particular, the proximal segment A is formed of a first section 24 having a cross section illustrated in FIG. 2, a second section 26 of transition, and a third section 28 having a cross section illustrated in FIG. 3. The first section 24 includes an extruded tubular wall 32 of a first material having a plurality of strands 34 of a second material coextruded with and surrounded by the wall material. The strands 34 are formed of a material which is different from the first tubular wall material and has a stiffness which is greater than the stiffness of the wall material. The first section also has a outer diameter which is about 0.020 inches or greater (about 0.05 cm or greater), preferably between about 0.035 and 0.040 inches (about 0.089 to 0.102 cm) and a lumen diameter which is about 0.005 inches or greater (about 0.0127 cm or greater), preferably between about 0.015 and 0.020 inches (about 0.0381 to 0.051 cm). The first section or distal most portion of the proximal segment A can be relatively large because this portion is general positioned outside of the body or inside large diameter blood vessels.

The third section 28 of the proximal segment A includes a tubular wall 32 of the first material without any of the strands 32 which are present in the first section. The second section 26 which is provided between the first and third sections 24, 28 is a transition section between the first and third sections having a continuous gradually changing microcatheter confirmation. Accordingly, there are no distinct or visible boundaries between any of the three sections 24, 26, 28 of the proximal segment A. The proximal segment A has a static burst strength of at least 160 psi (at least 11.25 kg/cm$^2$), preferably at least 175 psi (at least 12.30 kg/cm$^2$), and a dynamic burst strength of at least 250 psi (at least 17.57 kg/cm$^2$), preferably 1200 psi (at least 84.36 kg/cm$^2$).

In the second section 26 or transition section, the strands 34 are gradually tapered out from a full size illustrated in FIG. 2 until they disappear completely. This gradual tapering is achieved by a co-extrusion process by which the strands gradually decrease in diameter until they disappear. The strands 34 may be large enough at the first section 24 that they melt together to form a ring. A microcatheter segment in which a flexibility of the microcatheter is continuously changing along the length of the segment due to the tapering of strands 34 within the microcatheter walls 32 is described in further detail in U.S. Provisional Patent Application Ser. No. 60/093,063 (converted to provisional application from Ser. No. 08/850,953), filed May 5, 1997 and Ser. No. 09/048,007 (Attorney Docket No. 018413-114), filed Mar. 26, 1998, now U.S. Pat. No. 5,976,120 issued Nov. 2, 1999, both of which are incorporated herein by reference in their entirety.

The distal segment B of the microcatheter according to the present invention also has three sections including, a first section 40 illustrated in cross section in FIG. 4, a second tapering section 42, and a third section 44 illustrated in cross section in FIG. 5. As shown in FIGS. 4 and 5, the distal segment B is formed along its entire length with an inner layer 46 and an outer layer 48. The inner layer 46 is formed of a DMSO or other solvent compatible material while the outer layer 48 is formed of a material having a greater strength and flexibility than the inner layer.

The high strength of the outer layer 48 provides the ability to resist high pressures of injection without bursting and the ability to resist tensile forces. The outer layer 48 also has a greater flexibility than the inner layer and allows the distal tip of the microcatheter to be directed by the flow of blood by allowing the microcatheter tip to bend easily in the direction that the blood is flowing. The outer layer 48 is preferably DMSO or other solvent compatible.

The flexibility of the outer layer 48 also provides the ability for the tip to oscillate when saline or a contrast agent is injected through the lumen. The oscillation of the flexible distal tip due to fluid injection allows the microcatheter to be advanced into a branch blood vessel by a coordinated oscillation and push when the blood flow fails to direct the tip into a branch vessel leading to the treatment site. The flexibility of the outer layer 48 also provides the microcatheter with an ability to bend or to turn a corner when pushed against a blood vessel wall.

The first section 40 of the proximal segment B of the microcatheter has an outer diameter substantially the same as an outer diameter of the distal end of the proximal segment A. The second section 42 is a tapered section in which the outer diameter of the microcatheter tapers from the diameter of the first section 40 to a smaller outer diameter of the third section 44 to provide increasing flexibility of the microcatheter toward the distal tip. The third section 44 of the distal segment B has a small outer diameter which allows the microcatheter to achieve the distal tip flexibility needed for a flow directed microcatheter.

The first section 40 of the proximal segment B has a outer diameter which is between about 0.020 and 0.050 inches (about 0.05 and 0.127 cm), preferably between about 0.030 and 0.035 inches (about 0.076 and 0.089 cm) and a lumen diameter which is between about 0.005 and 0.030 inches (about 0.0127 and 0.076 cm), preferably between about 0.014 and 0.018 inches (about 0.0356 and 0.0457 cm). The third section 44 of the proximal segment has an outer diameter which is approximately ⅔ of the outer diameter of the first section 40. The third section 44 has an outer diameter between about 0.010 and 0.030 inches (about 0.0254 and 0.0762 cm), preferably between about 0.020 and 0.025 inches (about 0.05 and 0.0635 cm), and an inner lumen diameter of between about 0.005 and 0.020 inches (about 0.0127 and 0.05 cm), preferably between about 0.010 and 0.015 inches (about 0.025 and 0.038 cm). The inner layer 46 and the outer layer 48 preferably have approximately equal thickness which decrease together between the first section 40 and the third section 44. The distal segment B has a static burst strength of at least 140 psi (at least 965 kPa), and preferably at least 175 psi (at least 1205 kPa).

The fused joint 12 between the proximal segment A and the distal segment B of the microcatheter according to the present invention is preferably formed by heat fusing the different materials of the two segments together. However, when heat fusing is used between microcatheter segments of different materials and sizes, the resulting joint is often prone to kinking. The kinking problem of fuse joints is due to the fact that one of the tube segments is more flexible than the other and the flexing of the tube at the joint is therefore concentrated at an end of the more flexible tube causing the more flexible tube to kink.

The present invention addresses this problem of kinking by forming the third section 28 of the proximal segment A and the first section 40 of the distal segment B with very similar properties of flexibility. In particular, the third section 28 of the proximal segment A and the first section 40 of the distal segment B are formed from materials having durometers which are substantially the same and having inner and outer dimensions which are substantially the same. For example, the outer diameters can vary by approximately 20 percent or less. The durometers of the proximal segment A and the distal segment B adjacent the joint 12 vary by less than about 40 percent, preferably less than 20 percent. This similarity in stiffness and size provides of the two segments at the joint 12 a very gradual transition at the fused joint 12 between the proximal and distal segment and inhibits kinking.

The microcatheter 10 of the present invention is preferably coated with an exterior lubricous or hydrophilic coating over the proximal and distal segments A, B to assist in tracking the microcatheter through the vasculature. An internal lubricous or hydrophilic coating may also be used. The coating used on the microcatheter according to the present invention may be any of the coatings known to those in the art, such as hydrophilic and hydrophobic coatings and is preferably a DMSO compatible coating material. In order to provide the extra flexible or floppy distal tip of the microcatheter needed for flow directed insertion of the microcatheter 10, a portion of the third section 44 of the distal segment B is preferably left uncoated. Preferably, about 1–8 cm of the distal tip are left uncoated. A distal tip of a flow directed microcatheter is sufficiently flexible for flow directed insertion when the flexibility of the tip allows the tip to bend when directed by a flow of blood and to oscillate when saline or another fluid is injected through the lumen.

The microcatheter 10 according to the present invention preferably includes a radiopaque marker 52 at a distal tip as shown in FIG. 6 to provide visibility of the tip location under X-ray or fluoroscopy. The marker 52 is positioned within about 1 cm from the tip, and preferably approximately 1 mm from the tip. The marker may be formed of any one of the known marker materials in a generally known manner. Examples of suitable marker material include, for instance, gold, platinum, or a combination of the two.

The following example is offered for illustrative purposes only and is not to be construed in any way as limiting the scope of the present invention. Unless otherwise stated, all temperatures are in degrees Celsius. In this example, the following abbreviations have the following meanings and, if not defined, the abbreviation has its accepted meaning:

cm = centimeter $cm^2$ = square centimeter

DMSO = dimethylsulfoxide kg = kilogram psi = pounds per square inch

EXAMPLE

One example of a microcatheter according to the present invention includes a proximal segment A formed of polyester elastomer wall material 32, such as Hytrel (available from New England Urethane and General Polymers), with polyester elastomer strands 34 having a higher durometer than the polyester elastomer of the walls. The polyester elastomer wall material 32 has a durometer of about 30 Shore D, while the strand material 34 has a durometer of about 82 Shore D. The proximal segment A preferably has a burst strength of approximately 160 psi or greater (11.25 $kg/cm^2$) and is coextruded. A length L1 of the first section 24 may vary from about 100 cm to about 150 cm. The second transition section 26 in which the stiff strand material is gradually blended out has a length L2 of approximately 5 to 40 cm, preferably between 10 and 25 cm. The third section 28 which is formed entirely of the polyester elastomer material of the walls 32 without the strands 34 has a length L3 of approximately 10 to 40 cm. The proximal segment A has a substantially constant outer diameter of about 0.038 inches and a substantially constant inner diameter of about 0.010 inches along the length of the proximal segment.

The distal segment B according to this example is formed with the inner layer 46 of a chlorinated polyolefin, such as Alcryn (available from Advanced Polymer Alloys), and an outer layer 48 of a polyvinyl chloride. The distal segment B preferably has a burst strength of approximately 140 psi (9.84 $kg/cm^2$) or greater. The chlorinated polyolefin is DMSO compatible while the outer layer of polyvinyl chloride is not DMSO compatible. The distal segment B has a total length of between about 10 and 40 cm and includes a first section 40 having a length L4 of between about 10 and 20 cm, a second tapered section 42 having a length L5 of about 5 to 15 cm, and a third section 44 or distal tip having a length L6 of about 20 to 30 cm. The distal segment B tapers from an outer diameter of about 0.033 inches at the first section 40 to an outer diameter of about 0.022 inches at the third section 44. The inner diameter of the distal segment also tapers from an inner diameter of about 0.016 inches at the first section 40 to an inner diameter of about 0.012 inches at the third section 44.

The microcatheter according to this example is coated with a lubricous or hydrophilic coating which is provided on the interior and exterior of the entire microcatheter except for approximately the distal most 2–10 cm of the microcatheter.

In use, the microcatheter according to the present invention will normally be used without a guidewire, however a guidewire may be used for insertion of the microcatheter. Particularly, a guidewire may be used to insert the microcatheter through guidewire steering to a region of the body where treatment is to be performed and the microcatheter may thereafter be flow directed to the particular target site.

The flow directed microcatheter is directed to the target site within a blood vessel by one of the techniques of 1) allowing the distal tip to follow the flow of blood through the vasculature while pushing to advance the catheter, 2) injecting small pulses of saline or other fluid through the catheter to cause the distal tip of the catheter to oscillate coordinated with a push of the catheter, or 3) a combination of the two techniques.

The microcatheters according to the present invention may be manufactured using various known extrusion methods. Known methods of co-extrusion, including cross header arrangements, over-extrusion, and extrusion die construction may be applied to manufacture the microcatheters. Strand thickness, wall thickness, diameter and relative percentage of composition can be controlled with known techniques including speed controlled extrusion, throttled flow controlled extrusion, waste-gating and other known methods. The several materials mentioned for use in the microcatheters have proven useful, but it is expected that new and better materials will be applied in the construction of the inventions described above.

While the invention has been described in detail with reference to the preferred embodiments thereof, it will be apparent to one skilled in the art that various changes and modifications can be made and equivalents employed, without departing from the present invention.

What is claimed is:

1. A flow directed microcatheter comprising:
a proximal segment having a first end, a second end, and a lumen extending along a length of the proximal segment between the first and second ends, the proximal segment having a substantially constant outer diameter and a substantially constant inner diameter along the length of the proximal segment, and the proximal segment having a flexibility which changes between the first and second ends without distinct joints between the first and second ends, wherein the proximal segment includes a base material and a strengthening material formed in strands which decrease in diameter toward the second end of the proximal segment;
a hub connected to the first end of the proximal segment;
a distal segment having a first end, a second end, and a lumen extending along a length of the distal segment between the first and second ends, the distal segment having an inner layer formed of a first material and an outer layer formed of a second material having a higher burst strength than that of the inner layer, the distal segment tapering from a first diameter at the first end to a second diameter at the second end, wherein a flexibility of the distal segment allows the microcatheter to be guided by a flow of blood or oscillation of the second end by injection of fluid through the lumens without the use of a guidewire; and
a joint formed between the second end of the proximal segment and the first end of the distal segment.

2. The flow directed microcatheter according to claim 1, wherein the proximal segment is formed of a DMSO compatible material.

3. The flow directed microcatheter according to claim 1, wherein the first material and the second material of the distal segment are DMSO compatible materials.

4. The flow directed microcatheter according to claim 1, wherein the proximal segment has a flexibility at the second end which is greater than a flexibility at the first end.

5. The flow directed microcatheter according to claim 1, wherein the distal segment includes an inner layer of a chlorinated polyolefin and an outer layer of polyvinyl chloride.

6. The flow directed microcatheter according to claim 1, wherein the proximal segment is formed of polyester elastomer.

7. A flow directed microcatheter comprising:
a proximal segment having a first end, a second end, and a lumen extending along a length of the proximal segment between the first and second ends, the proximal segment having a substantially constant outer diameter and a substantially constant inner diameter along the length of the proximal segment, and the proximal segment having a flexibility which changes between the first and second ends without distinct joints between the first and second ends;
a hub connected to the first end of the proximal segment;
a distal segment having a first end, a second end, and a lumen extending along a length of the distal segment between the first and second ends, the distal segment having an inner layer formed of a first material and an outer layer formed of a second material having a higher burst strength than that of the inner layer, the distal segment tapering from a first diameter at the first end to a second diameter at the second end, wherein a flexibility of the distal segment allows the microcatheter to be guided by a flow of blood or oscillation of the second end by injection of fluid through the lumens without the use of a guidewire;
a joint formed between the second end of the proximal segment and the first end of the distal segment; and
wherein the proximal segment includes a first polyester elastomer having a first durometer, and a second polyester elastomer having a second durometer which is formed in a plurality of tapering strands within a wall of the microcatheter.

8. A flow directed microcatheter comprising:
a proximal segment having a first end, a second end, and a lumen extending along a length of the proximal segment between the first and second ends, the proximal segment formed of a material which is compatible with DMSO;
a distal segment having a first end, a second end, and a lumen extending between the first and second ends, the first end of the distal segment connected to the second end of the proximal segment, the distal segment including:
an inner layer formed of a first material which is compatible with DMSO, the inner layer having an inner layer flexibility and an inner layer strength; and
an outer layer formed of a second material having an outer layer flexibility and an outer layer strength which are greater than the inner layer flexibility and the inner layer strength; and
wherein the proximal segment and the distal segment are coated with a hydrophilic coating and a portion of the second end of the distal segment forming a microcatheter distal tip is uncoated to improve flexibility of the microcatheter distal tip.

9. The flow directed microcatheter according to claim 8, wherein the first material is a chlorinated polyolefin.

10. The flow directed microcatheter according to claim 9, wherein the second material is polyvinyl chloride.

11. The flow directed microcatheter according to claim 8, wherein the first material and the second material are coextruded and the distal segment tapers from a first diameter at the first end to a second diameter at the second end.

12. A microcatheter comprising:
a first segment having a first end, a second end, and lumen extending along a length of the first segment between the first and second ends;
a second segment having a first end, a second end, and a lumen extending along a length of the second segment between the first and second ends, wherein the first segment includes a base material and a strengthening material formed in strands which decrease in diameter toward the second end of the first segment; and
a joint formed between the second end of the first segment and the first end of the second segment.

13. A flow directed microcatheter comprising:
a catheter segment having a first end, a second end, and a lumen extending between the first and second ends, wherein a flexibility of the catheter segment increases towards the second end to allow the microcatheter to be flow directed, wherein the catheter segment is coated with a hydrophilic coating and a portion of the second end forming a microcatheter distal tip is uncoated to improve flexibility of the microcatheter distal tip.

* * * * *